(12) United States Patent
Hashimoto et al.

(10) Patent No.: US 9,029,724 B2
(45) Date of Patent: May 12, 2015

(54) MICROPARTICLE SORTING DEVICE AND METHOD FOR CONTROLLING POSITION IN MICROPARTICLE SORTING DEVICE

(71) Applicant: Sony Corporation, Tokyo (JP)

(72) Inventors: Gakuji Hashimoto, Tokyo (JP); Akiko Tsuji, Kanagawa (JP); Yosuke Muraki, Tokyo (JP); Kouhei Hatamoto, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/118,994

(22) PCT Filed: Feb. 4, 2013

(86) PCT No.: PCT/JP2013/052467
§ 371 (c)(1),
(2) Date: Nov. 20, 2013

(87) PCT Pub. No.: WO2013/145862
PCT Pub. Date: Oct. 3, 2013

(65) Prior Publication Data
US 2014/0144817 A1 May 29, 2014

(30) Foreign Application Priority Data

Mar. 30, 2012 (JP) ................................ 2012-081056

(51) Int. Cl.
*G01N 15/14* (2006.01)
(52) U.S. Cl.
CPC ...... *G01N 15/1425* (2013.01); *G01N 2015/149* (2013.01); *G01N 15/14* (2013.01); *Y10S 209/908* (2013.01)
(58) Field of Classification Search
CPC ................. G01N 15/1425; G01N 2015/0019; G01N 15/0205; G01N 15/0227; G01N 15/0288; G01N 2015/0637; G01N 2015/1006; G01N 2015/1081; G01N 15/14; G01N 2015/149; G01N 33/48; G01N 33/50; G01N 37/00
USPC .............. 209/552, 127.1, 128, 576, 638, 908; 436/63, 164; 422/73, 82.05
See application file for complete search history.

(56) References Cited

U.S. PATENT DOCUMENTS

2010/0315639 A1* 12/2010 Muraki ......................... 356/342
2011/0284378 A1* 11/2011 Shinoda ........................ 204/603
(Continued)

FOREIGN PATENT DOCUMENTS

JP    2002-505423    2/2002
JP    2002-521658    7/2002
(Continued)

*Primary Examiner* — David H Bollinger
(74) *Attorney, Agent, or Firm* — Wolf, Greenfield & Sacks, P.C.

(57) ABSTRACT

A microparticle sorting device that automatically and accurately adjusts the positions of a fluid stream and a collection container is provided.

The microparticle sorting device including a pair of deflecting plates that face each other with a passage area of a fluid stream therebetween, a camera that captures the image of the fluid stream, and a fluid stream detection light source that emits light parallel to a direction in which the deflecting plates face each other and that is movable in a direction perpendicular to the fluid stream and the light is provided. In the microparticle sorting device, the collection container that receives the fluid stream is mounted so as to be movable in the direction perpendicular to the fluid stream and the light.

11 Claims, 9 Drawing Sheets

(56) References Cited

U.S. PATENT DOCUMENTS

| | | |
|---|---|---|
| 2012/0200857 A1* | 8/2012 | Sharpe et al. ............... 356/436 |
| 2013/0256136 A1 | 10/2013 | Muraki et al. |
| 2013/0258075 A1 | 10/2013 | Muraki et al. |
| 2014/0174206 A1* | 6/2014 | Akiyama et al. ............. 73/863 |
| 2014/0193059 A1 | 7/2014 | Muraki |
| 2014/0208875 A1 | 7/2014 | Muraki |

FOREIGN PATENT DOCUMENTS

| | | |
|---|---|---|
| JP | 2010-190680 | 9/2010 |
| JP | 2010-286292 | 12/2010 |
| JP | 2010-286341 | 12/2010 |
| JP | 2011-237201 | 11/2011 |
| WO | WO 2010/095391 A1 | 8/2010 |

* cited by examiner

MICROPARTICLE SORTING DEVICE AND METHOD FOR CONTROLLING POSITION IN MICROPARTICLE SORTING DEVICE

TECHNICAL FIELD

The present technology relates to a microparticle sorting device and a method for controlling a position in a microparticle sorting device and, in particular, to, for example, a microparticle sorting device automatically adjusting the position of a fluid stream generated from an orifice and the position of a collection container that receives the fluid stream.

BACKGROUND ART

Microparticle sorting device that optically, electrically, or magnetically detects the characteristics of microparticles, such as cells, and sorts and collects only the microparticles having a predetermined characteristic have been known (e.g., a flow cytometer).

In cellular fractionation performed by the flow cytometer, the fluid stream (the laminar flow of a sample fluid and a sheath fluid) is generated by an orifice formed in a flow cell. By applying vibration to the orifice, the fluid stream is converted into droplets, and electrical charge is imparted to the droplets. Thereafter, by electrically controlling the direction in which each of the droplets including a cell ejected from the orifice moves, a target cell having a desired characteristic and a non-target cell are collected into different collection containers.

For example, PTL 1 describes "a microparticle sorting device including a microchip having a flow path that allows fluid including microparticles to flow therethrough and an orifice that ejects the fluid flowing through the flow path, a vibrating element for converting the fluid into droplets at the orifice, charging means for imparting electrical charge to the ejected droplets, optical detection means for detecting the optical characteristics of the microparticles that flow through the flow path, a pair of electrodes that are disposed in the moving direction of the droplets ejected into a space outside the chip and that face each other with the moving droplets therebetween, and at least two containers for collecting the droplets that have passed between the electrodes" and serving as a microchip type flow cytometer.

CITATION LIST

Patent Literature

PTL 1: Japanese Unexamined Patent Application Publication No. 2010-190680

SUMMARY OF INVENTION

Technical Problem

In microparticle sorting devices, in order for the fluid stream generated from an orifice formed in the flow cell or a microchip to accurately enter the collection container, it is required to adjust the position of the flow cell or microchip to align the positions of the fluid stream and the collection container. If the position adjustment is improper, the droplets including the microparticles do not enter the collection container and, thus, sorting of the microparticles is not available, or the amount of collection is decreased. In addition, if the droplets including cells does not accurately drop onto the center of the collection container, the cell collide with the inner wall of the collection container and are damaged. Accordingly, the surviving rate of the cells decreases.

In existing methods, the position adjustment is performed by a user who adjusts the positions of the flow cell and the microchip by hand while viewing the position of the fluid stream. Accordingly, the user needs to be proficient in the operation and, thus, a problem of the reliability and stability arises. In addition, each time the flow cell or the microchip is replaced with a new one, the alignment that is significantly troublesome is required.

Accordingly, it is a main object of the present technology to provide a microparticle sorting device that automatically and accurately adjust the positions of the flow cell and the microchip.

Solution to Problem

To solve the above-described problem, the present technology provides a microparticle sorting device including a pair of deflecting plates that face each other with a passage area of a fluid stream therebetween, a camera that captures an image of the fluid stream, and a fluid stream detection light source that emits light parallel to a direction in which the deflecting plate faces each other and that is movable in a direction perpendicular to the fluid stream and the light. In the microparticle sorting device, a collection container that receives the fluid stream can be mounted so as to be movable in the direction perpendicular to the fluid stream and the light.

The microparticle sorting device further includes a control unit that detects a bright point in an image captured by the camera by image recognition and stores the position of the fluid stream detection light source obtained when the image having the detected bright point therein is captured. In the microparticle sorting device, since the control unit adjusts the position of the collection container on the basis of the position of the fluid stream detection light source obtained when the image having the detected bright point therein is captured, the position of the fluid stream generated from the orifice and the position of the collection container can be automatically adjusted.

In the microparticle sorting device, the control unit may be configured to move the fluid stream detection light source in the direction perpendicular to the fluid stream and the light until the bright point is detected in an image captured by the camera. In addition, a plurality of the fluid stream detection light sources may be disposed so as to be separated from each other in the direction of the fluid stream.

In the microparticle sorting device, an orifice that generates the fluid stream may be configured as a microchip type flow cytometer provided in a microchip.

Furthermore, the present technology provides a method for adjusting a position of a fluid stream and a position of a collection container for use in a microparticle sorting device. The method including the steps of emitting light that is parallel to a direction in which a pair of deflecting plates that face each other with a passage area of a fluid stream therebetween face each other while moving the light in a direction perpendicular to the fluid stream and the light, acquiring an image of the fluid stream, detecting a bright point in the image by image recognition, and adjusting the position of the collection container that receives the fluid stream in the direction perpendicular to the fluid stream and the light on the basis of an irradiation position of the light when the image having the detected bright point therein is acquired.

According to the present technology, the term "microparticle" widely refers to a biologically-relevant microparticle, such as a cell, a microorganism, or a liposome, or a synthetic particle, such as a latex particle, a gel particle, or an industrial particle.

Examples of the biologically-relevant microparticle include a chromosome, a liposome, a mitochondria, and an organelle that form a variety of cells. Examples of the cell include an animal cell (e.g., a blood cell) and a plant cell. Examples of microorganism include bacteria (e.g., bacteria coliform), viruses (e.g., a tobacco mosaic virus), and fungi (e.g., a yeast cell). In addition, examples of the biologically-relevant microparticle can include a biologically-relevant high molecule, such as nucleic acid, protein, or a complex thereof. Furthermore, examples of the industrial particle include an organic or inorganic high-polymer material and a metal. Examples of the organic high-polymer material include polystyrene, styrene, divinylbenzen, and polymethylmethacrylate. Examples of the inorganic high-polymer material include glass, silica, and magnetic material. Examples of the metal include gold colloid and aluminum. In general, these microparticles are spherical in shape. However, these microparticles may be non-spherical in shape. In addition, these microparticles may have any sizes and masses.

Advantageous Effects of Invention

The present technology provides a microparticle sorting device that automatically and accurately adjusts the positions of the fluid stream and the collection container.

DESCRIPTION OF EMBODIMENTS

Figure 1:
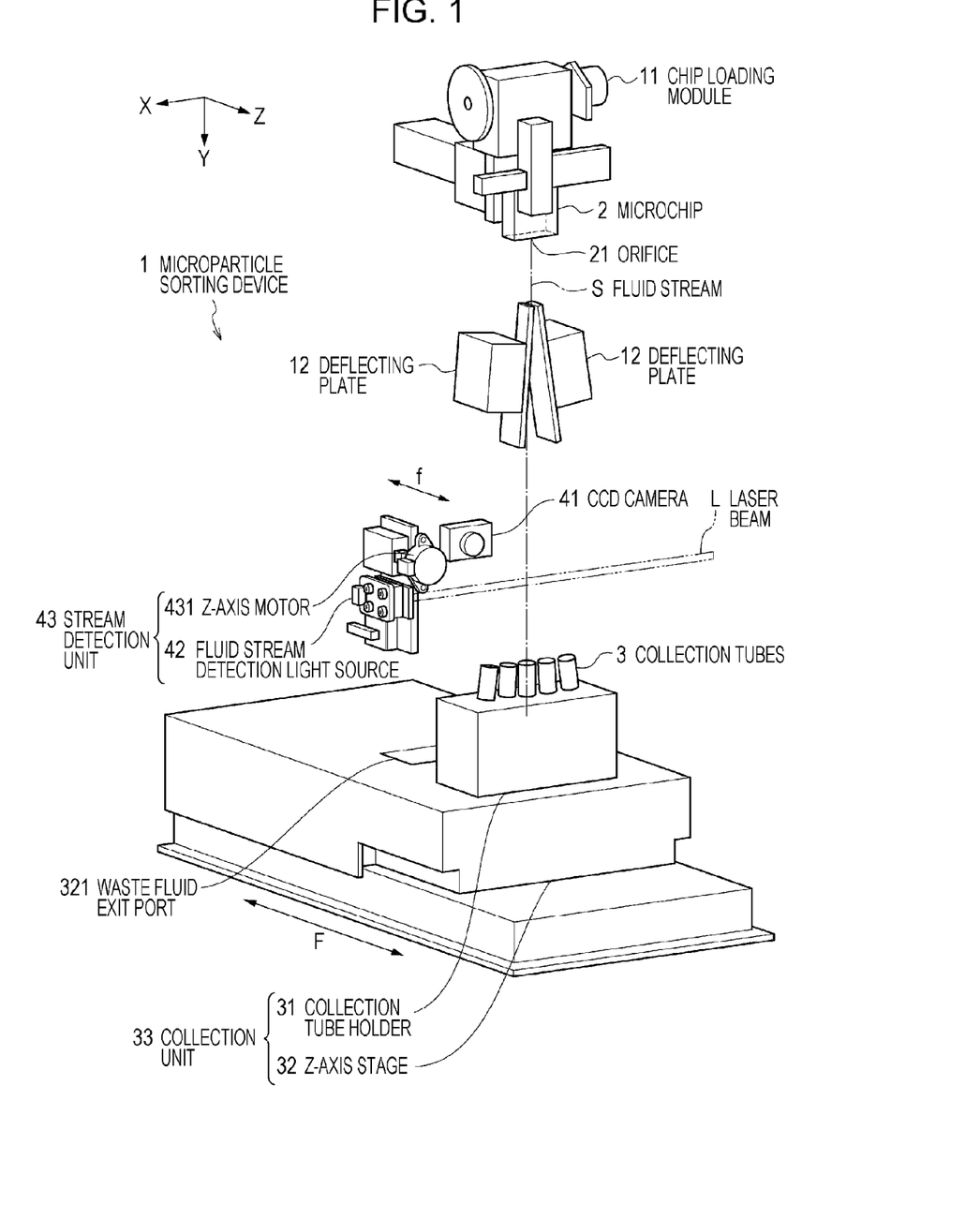
FIG. 1 is a schematic illustration of the configuration of a sorting system of a microparticle sorting device 1 (a flow cytometer 1) configured as a microchip type flow cytometer according to a first embodiment of the present technology.

Exemplary embodiments of the present technology are described below with reference to the accompanying drawings. Note that the embodiments described below are only typical examples of the present technology and, therefore, do not narrow the scope of the present technology. The descriptions are made in the following order:

1. Device Configuration of Microparticle Sorting Device According to First Embodiment
(1-1) Chip Loading Module
(1-2) Microchip
(1-3) Deflecting Plate
(1-4) Collection Unit
(1-5) Stream Detection Unit
(1-6) Control Unit and Others
2. Position Control Performed by Microparticle Sorting Device According to First Embodiment
(2-1) Collection Unit Position Initialization Step $S_1$
(2-2) Fluid Stream Generation Step $S_2$
(2-3) Stream Detection Unit Z-Axis Scanning/Fluid Stream Imaging Step $S_3$
(2-4) Image Recognition Step $S_4$
(2-5) Detected Position Storing Step $S_5$
(2-6) Z-Axis Stage Movement/Position Adjustment Step $S_6$
3. Device Configuration of Microparticle Sorting Device According to Embodiment Related to Present Technology
4. Position Control Performed by Microparticle Sorting Device According to Related Embodiment
(4-1) Collection Unit Position Initialization Step $S_1$/Fluid Stream Generation Step $S_2$
(4-2) Fluid Stream Imaging Step $S_3$
(4-3) Image Recognition/Angle $\theta$ Detection Step $S_4$
(4-4) Z-Axis Stage Movement/Position Adjustment Step $S_5$ 1. Device Configuration of Microparticle Sorting Device According to First Embodiment FIG. 1 is a schematic illustration of the configuration of a sorting system of a microparticle sorting device 1 (hereinafter also referred to as a "flow cytometer 1") configured as a microchip type flow cytometer according to a first embodiment of the present technology.

(1-1) Chip Loading Module

In the drawing, a reference numeral 11 represents a chip loading module that holds a microchip 2. The chip loading module 11 includes a chip loading unit that delivers the microchip 2 inserted from the outside to a predetermined position and hold the microchip 2 and a fluid sending connector unit that supplies, for example, sample fluid including cells and sheath fluid to the microchip 2 that is held (neither is shown). In addition, the chip loading module 11 includes a chip vibrating unit and a charging unit (neither is shown). The chip vibrating unit applies vibration to an orifice 21 that is formed in the microchip 2 to generate a laminar flow of the sample fluid and the sheath fluid (a fluid stream S) and causes the orifice 21 to eject droplets of the fluid stream S. The charging unit imparts electrical charge to the ejected droplets.

(1-2) Microchip

Figure 2:
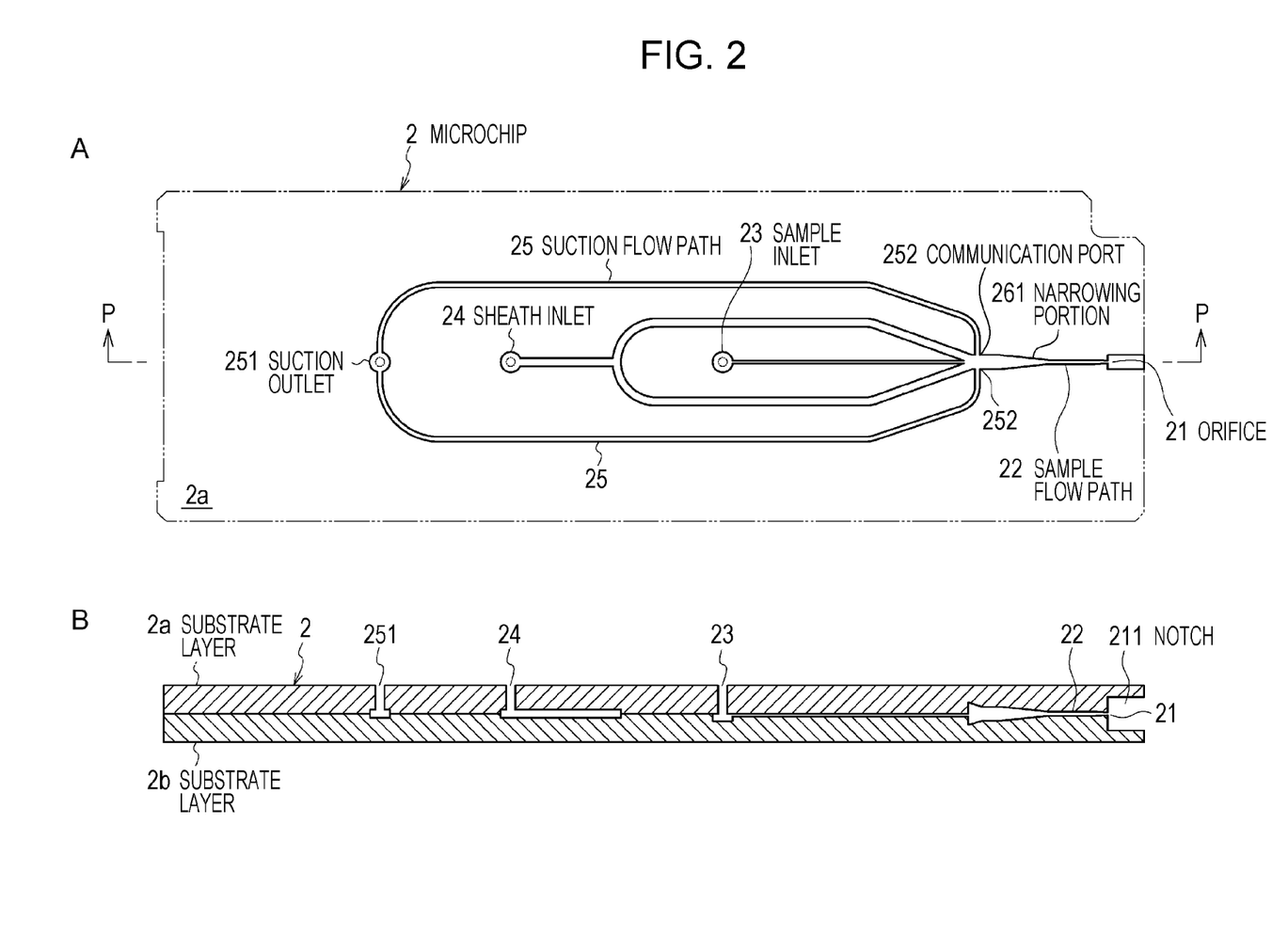
FIG. 2 illustrates the configuration of an example of a microchip 2 mountable in the flow cytometer 1.
Figure 3:
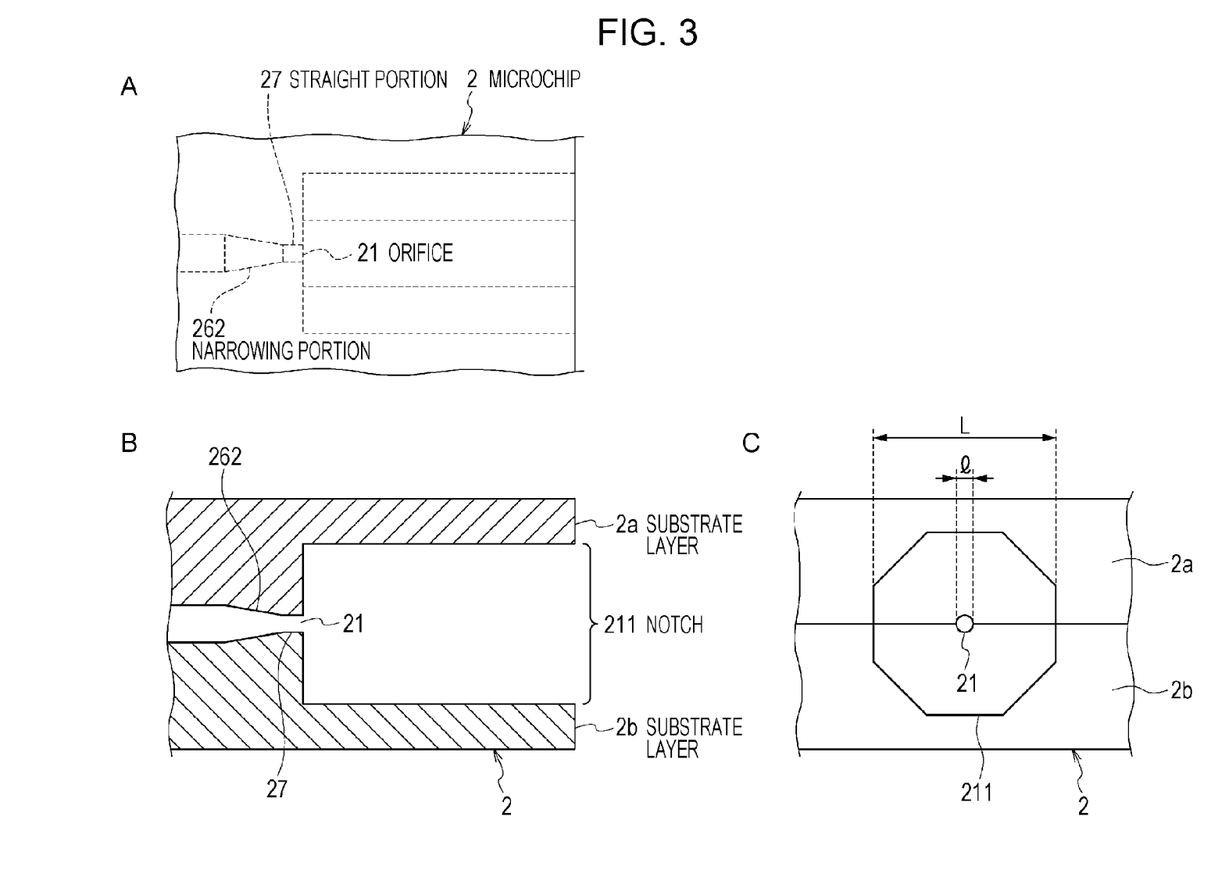
FIG. 3 is a schematic illustration of the configuration of an orifice 21 of the microchip 2.

FIGS. 2 and 3 illustrate an example of the microchip 2 mountable in the flow cytometer 1. FIG. 2A is a schematic illustration of the top surface, and FIG. 2B is a schematic illustration of a cross section corresponding to a P-P cross section of FIG. 2A. In addition, FIG. 3 schematically illustrates the structure of the orifice 21 of the microchip 2, where FIG. 3A is a top view, FIG. 3B is a cross-sectional view, and FIG. 3C is a front view. FIG. 3B corresponds to the P-P cross section of FIG. 2A.

The microchip 2 is formed by bonding substrate layers 2a and 2b having a sample flow path 22 formed therein. The sample flow path 22 can be formed in the substrate layers 2a and 2b by using injection molding of thermoplastic resin. Examples of the thermoplastic resin include plastics that are well-known as a material of existing microchips, such as polycarbonate, polymethylmethacrylate resin (PMMA), cyclic polyolefin, polyethylene, polystyrene, polypropylene, and polymethyldisilazane (PDMS).

The sample fluid is introduced from the fluid sending connector unit to a sample inlet 23. Thereafter, the sample fluid merges with the sheath fluid introduced from the fluid sending connector unit to a sheath inlet 24 and is delivered to the sample flow path 22. The sheath fluid introduced from the sheath inlet 24 branches in two directions and is delivered. Thereafter, the sheath fluid merges with the sample fluid so as to sandwich the sample fluid in two directions at a merge point at which the sheath fluid merges with the sample fluid introduced from the sample inlet 23. In this manner, a three-dimensional laminar flow in which the sample fluid laminar flow is located at the center of the sheath fluid laminar flow is formed.

A reference numeral 25 represents a suction flow path used for, if clogging occurs or bubbles are generated in the sample flow path 22, eliminating the clogging or the bubbles by applying a negative pressure to the inside of the sample flow path 22 and temporarily causing the sample fluid to flow backward. The suction flow path 25 has a suction outlet 251 formed at one end. The suction outlet 251 is connected to a negative pressure source of, for example, a vacuum pump via the fluid sending connector unit. The other end is connected to the sample flow path 22 at a communication port 252.

The width of the three-dimensional laminar flow is narrowed in a narrowing portion 261 (refer to FIG. 2) and a narrowing portion 262 (refer to FIG. 3) each having the cross-sectional area that is perpendicular to a fluid delivery direction and that decreases from the upstream to downstream in the fluid delivery direction gradually or in a stepwise manner. Thereafter, the three-dimensional laminar flow is discharged from the orifice 21 formed at one end of the flow path in the form of a fluid stream S (refer to FIG. 1). In FIG. 1, the direction in which the fluid stream S is discharged from the orifice 21 is represented by a positive Y-axis direction.

The characteristics of a cell are detected between the narrowing portion 261 and the narrowing portion 262 of the sample flow path 22. For example, in optical detection, a laser beam is emitted from a light irradiation detecting unit (not shown) to cells flowing in single file through the core of the three-dimensional laminar flow in the sample flow path 22, and scattered light or fluorescence generated from each of the cells is detected by a light detector.

A connection portion of the sample flow path 22 to the orifice 21 is formed as a straight portion 27 extending in a line. The straight portion 27 functions to eject the fluid stream S from the orifice 21 straight in the positive Y-axis direction.

The fluid stream S ejected from the orifice 21 is converted into fluid droplets by vibration applied to the orifice 21 by the chip vibrating unit. The orifice 21 is open in the end surface direction of the substrate layers 2*a* and 2*b*. A notch 211 is provided between the opening position of the orifice 21 and the end surface of each of the substrate layers. The notch 211 is formed by cutting off the substrate layers 2*a* and 2*b* between the opening position of the orifice 21 and the end surface of each of the substrates so that a diameter L of the notch 221 is greater than the opening diameter l of the orifice 21 (refer to FIG. 3C). In order not to disturb the movement of the droplet ejected from the orifice 21, it is desirable that the diameter L of the notch 211 be greater than or equal to twice the opening diameter l of the orifice 21.

(1-3) Deflecting Plate

In FIG. 1, reference numerals 12, 12 represent two deflecting plates disposed so as to face each other with the fluid stream S (or the ejected droplets) ejected from the orifice 21 therebetween. The deflecting plates 12, 12 are configured to include electrodes for controlling the movement direction of the droplet ejected from the orifice 21 using an electrical force acting on the electrical charge imparted to the droplet. In addition, the deflecting plates 12, 12 control the trajectory of the fluid stream S generated from the orifice 21 using an electrical force acting on the electrical charge imparted to the fluid stream S. In FIG. 1, the direction in which the deflecting plates 12, 12 face each other is represented by an X-axis direction.

(1-4) Collection Unit

In the flow cytometer 1, the fluid stream S (or the droplet of the fluid stream S) is received from one of a plurality of collection tubes (the collection containers) 3 arranged in a line in the direction in which the deflecting plates 12, 12 face each other (the X-axis direction). The collection tubes 3 may be plastic tubes and glass tubes that are widely used for experiments. The number of the collection tubes 3 is not limited to any particular number. In this example, five collection tubes 3 are illustrated. The fluid stream S generated from the orifice 21 is led to one of the five collection tubes 3 in accordance with the presence of an electrical acting force between the deflecting plates 12, 12 or the magnitude of the force and is collected by the collection tube 3.

The collection tubes 3 are replaceably disposed in a collection tube holder 31. In addition, the collection tube holder 31 is disposed on a Z-axis stage 32 configured to be movable in a direction (a Z-axis direction) that is perpendicular to the direction in which the fluid stream S is emitted from the orifice 21 (the Y-axis direction) and that is perpendicular to the direction in which the deflecting plates 12, 12 face each other (the X-axis direction). In FIG. 1, an arrow F represents the direction in which the Z-axis stage 32 moves. In the drawing, a reference numeral 321 represents a waste fluid exit port provided in the Z-axis stage 32. In the flow cytometer 1, the collection tube holder 31 and the Z-axis stage 32 form a collection unit (a collection container moving stage unit) 33 that is driven by a Z-axis motor (not shown).

(1-5) Stream Detection Unit

The flow cytometer 1 includes a CCD camera 41 that captures the image of the fluid stream S. In addition, the flow cytometer 1 includes a stream detection unit 43. The stream detection unit 43 includes a fluid stream detection light source 42 that emits a laser beam L that is parallel to the direction in which the deflecting plates 12, 12 face each other (the X-axis direction) and a Z-axis motor 431 that moves the fluid stream detection light source 42 in a direction (a Z-axis direction) that is perpendicular to the direction in which the fluid stream S is ejected (the Y-axis direction) and that is perpendicular to the direction of the laser beam L (the X-axis direction). In FIG. 1, an arrow f indicates a direction in which the stream detection unit 43 moves. Note that the CCD camera 41 may be imaging means, such as a photoelectric conversion element (e.g., a line sensor or a single-plate photodiode). In addition to a laser source, such as an LED or an LD, xenon light or an incandescent lamp, for example, can be used as the fluid stream detection light source 42.

In the flow cytometer 1, due to individual difference in the microchip 2 mounted, the trajectory of the fluid stream S emitted from the orifice 21 varies. Each time the microchip 2 is replaced with a new one, the position of the fluid stream S in the Z-axis direction (and the X-axis direction) in the drawing may vary. Similarly, even for the same microchip 2, each time measurement is performed, the position of the fluid stream S may vary. The CCD camera 41, the stream detection unit 43, and the collection unit 33 function to detect such a change in position in the Z-axis direction (and the X-axis direction) and adjust the positions of the fluid stream S and the collection tubes 3 in the Z-axis direction.

(1-6) Control Unit and Others

In addition to the above-described configurations, the flow cytometer 1 includes a light irradiation detecting unit for detecting the optical characteristics of a cell, a data analyzing unit for determining the characteristics, a tank unit that stores the sample fluid and the sheath fluid, and a control unit for controlling such configurations, which widely used flow cytometers also include.

The control unit can be configured from a general-purpose computer including, for example, a CPU, a memory, and a hard disk. The hard disk stores, for example, an OS and a program that performs the steps of position control described below.

In addition, the light irradiation detecting unit includes an irradiation system and a detection system. The irradiation system includes a laser source, a light collecting lens or a dichroic mirror that collects and emits a laser beam onto a cell, and a bandpass filter. The detection system detects measurement target light generated from the cell in response to the emission of the laser beam. For example, the detection system is configured from, for example, a PMT (photo multiplier tube) or an area imaging element, such as a CCD or a CMOS element.

The measurement target light detected by the detection system of the light irradiation detecting unit is generated by a cell due to emission of the measurement light. For example, the measurement target light can be forward-scattered light, side scattered light, or one of scattered light and fluorescence of Rayleigh scattering or Mie scattering. Such measurement target light is converted into an electric signal, which is output to the control unit. In the control unit, the electric signal is used for determining the optical characteristics of the cell.

Note that the flow cytometer 1 may magnetically or electrically detect the characteristic of a cell. In this case, microelectrodes are disposed so as to face each other in the sample flow path 22 of the microchip 2 to measure, for example, the resistance value, the capacity value (the capacitance value), the inductance value, the impedance, the value of change in an electric field between the microelectrodes, a change in magnetization, a change in a magnetic field, or a change in a magnetic field.

Figure 4:
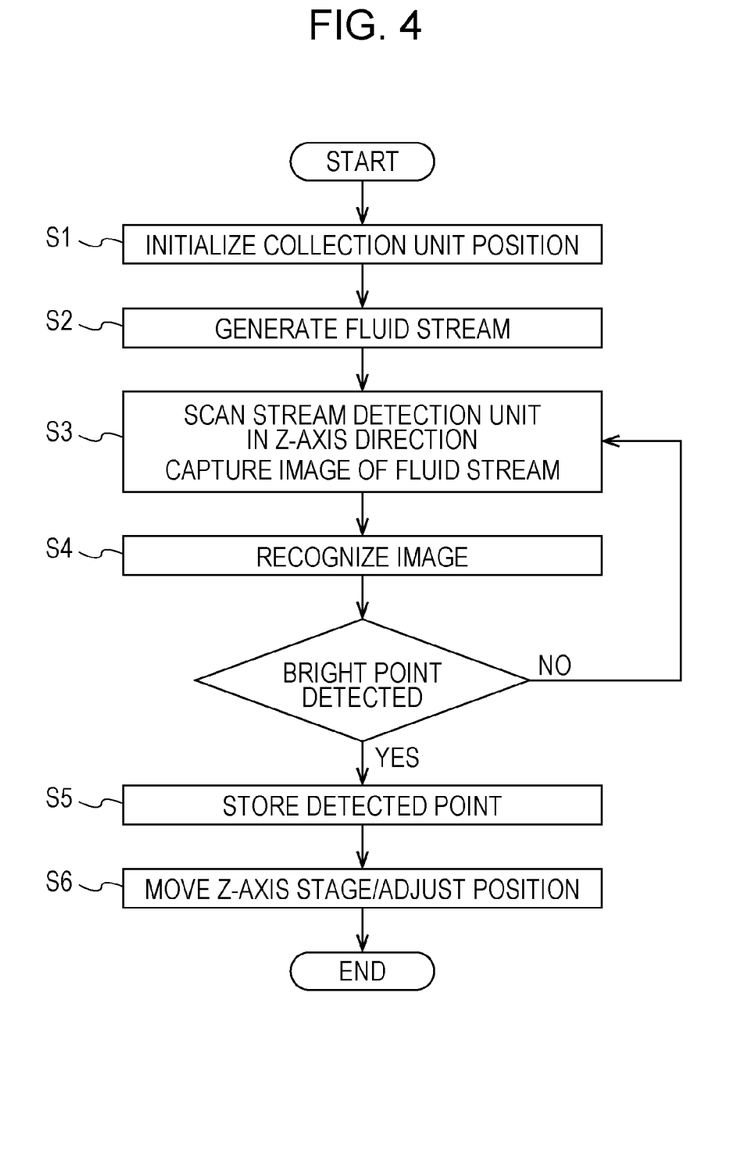
FIG. 4 is a flowchart illustrating a control step for adjusting the position of a fluid stream S and the position of a collection tube 3 in the flow cytometer 1.

2. Position Control Performed by Microparticle Sorting Device According to First Embodiment (2-1) Collection Unit Position Initialization Step $S_1$ FIG. 4 is a flowchart illustrating a control step for adjusting the position of the fluid stream S and the position of the collection tube 3 in the flow cytometer 1. The control step includes the procedures of "collection unit position initialization step $S_1$", "fluid stream generation step $S_2$", "stream detection unit Z-axis scanning/fluid stream imaging step $S_3$", "image recognition step $S_4$", "detected position storing step $S_5$", and "Z-axis stage movement/position adjustment step $S_6$". The procedures are described below.

First, in the collection unit position initialization step $S_1$, the position of the collection unit 33 is initialized. More specifically, the Z-axis stage 32 is moved in the Z-axis direction (refer to an arrow F in FIG. 1). The Z-axis stage 32 is moved to a position (an initialization position) at which the fluid stream S emitted from the orifice 21 enters the waste fluid exit port 321 provided in the Z-axis stage 32. The control unit outputs a signal to the Z-axis motor (not shown) to move the collection unit 33 to the initialization position.

(2-2) Fluid Stream Generation Step $S_2$

In step $S_2$, the fluid sending connector unit starts delivering the sample fluid and the sheath fluid to the sample inlet 23 and the sheath inlet 24 of the microchip 2, respectively, and the fluid stream S is emitted from the orifice 21. The control unit outputs a signal to the fluid sending connector unit to start delivering the sample fluid and the sheath fluid. The fluid stream S emitted from the orifice 21 is collected by the waste fluid exit port 321 and is discharged.

(2-3) Stream Detection Unit Z-axis Scanning/Fluid Stream Imaging Step $S_3$

In step $S_3$, the control unit causes the Z-axis motor 431 to move the stream detection unit 43 in the Z-axis direction (refer to the arrow f in FIG. 1). During the movement, the control unit captures the image of the fluid stream S using the CCD camera 41. Due to the movement of the stream detection unit 43, the fluid stream detection light source 42 is also moved in the Z-axis direction. Thus, the laser beam L emitted from the fluid stream detection light source 42 is scanned in the Z-axis direction.

(2-4) Image Recognition Step $S_4$

The image of the fluid stream S captured by the CCD camera 41 is output to the control unit, and the control unit detects a bright point in the image in the image recognition step $S_4$.

Figure 5:
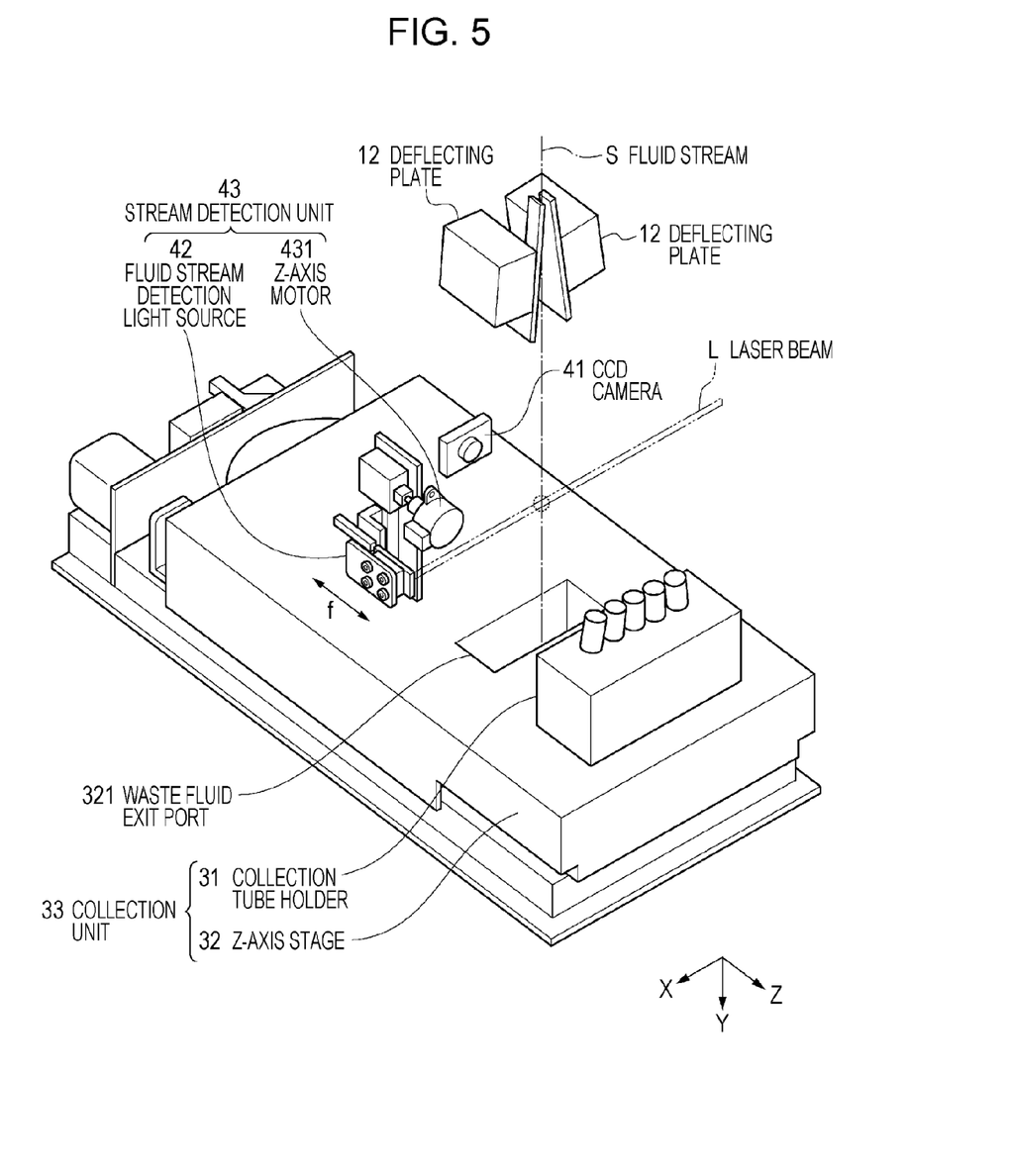
FIG. 5 schematically illustrates the position of a stream detection unit 43 when the laser beam L is located at the irradiation position of the fluid stream S in the flow cytometer 1.

When the stream detection unit 43 is moved in the Z-axis direction and the laser beam L is scanned in the same direction, the laser beam L is emitted to the fluid stream S at some position. FIG. 5 illustrates the position of the stream detection unit 43 when the laser beam L is located at the irradiation position of the fluid stream S.

If the laser beam L is located at the irradiation position of the fluid stream S, an irradiation point of the laser beam L in the fluid stream S is detected as a high-luminance pixel (a bright point) in the image of the fluid stream S captured by the CCD camera 41. However, if the laser beam L is not located at the irradiation position of the fluid stream S, a point at which the laser beam L is emitted in the fluid stream S does not appear. Accordingly, no bright point is detected in the image of the fluid stream S captured by the CCD camera 41.

That is, if a bright point is detected in the image of the fluid stream S, the stream detection unit 43 is located at the irradiation position of the laser beam L in the fluid stream S. The position of the stream detection unit 43 (the same as the position of the fluid stream detection light source 42) in the Z-axis direction corresponds to the position of the fluid stream S in the same direction.

While description has been made with reference to step $S_3$ in which the stream detection unit 43 is scanned in the Z-axis direction and step $S_4$ in which the position at which the laser beam L is emitted to the fluid stream S is detected, detection of the position may be made by moving the chip loading module 11 holding the microchip 2 in the Z-axis direction. In the case in which the chip loading module 11 is moved, the position of the stream detection unit 43 is predetermined so that the position of the laser beam L emitted from the fluid stream detection light source 42 is the same as the position of the collection tube 3 in the Z-axis direction. Note that when the chip loading module 11 is moved, the need for the following detected position storing step $S_5$ and Z-axis stage movement/position adjustment step $S_6$ may be eliminated.

(2-5) Detected Position Storing Step $S_5$

If a bright point is detected in the image of the fluid stream S, the control unit stores the position information of the stream detection unit 43 in the Z-axis direction as the position information of the fluid stream S in the same direction.

If no bright point is detected in the image of the fluid stream S, movement of the stream detection unit 43 in the Z-axis direction, capturing of the image of the fluid stream S (step $S_3$) using the CCD camera 41 and image recognition performed by the control unit (step $S_4$) are repeatedly performed. In this manner, the stream detection unit 43 is moved in the Z-axis direction until the laser beam L reaches the irradiation position in the fluid stream S and a bright point is detected in the image of the fluid stream S. Note that in the case in which the chip loading module 11 is moved, movement of the chip loading module 11 in the Z-axis direction, capturing of the image of the fluid stream S using the CCD camera 41, and image recognition performed by the control unit are repeatedly performed until a bright point is detected in the image of the fluid stream S.

(2-6) Z-axis Stage Movement/Position Adjustment Step $S_6$

Figure 6:
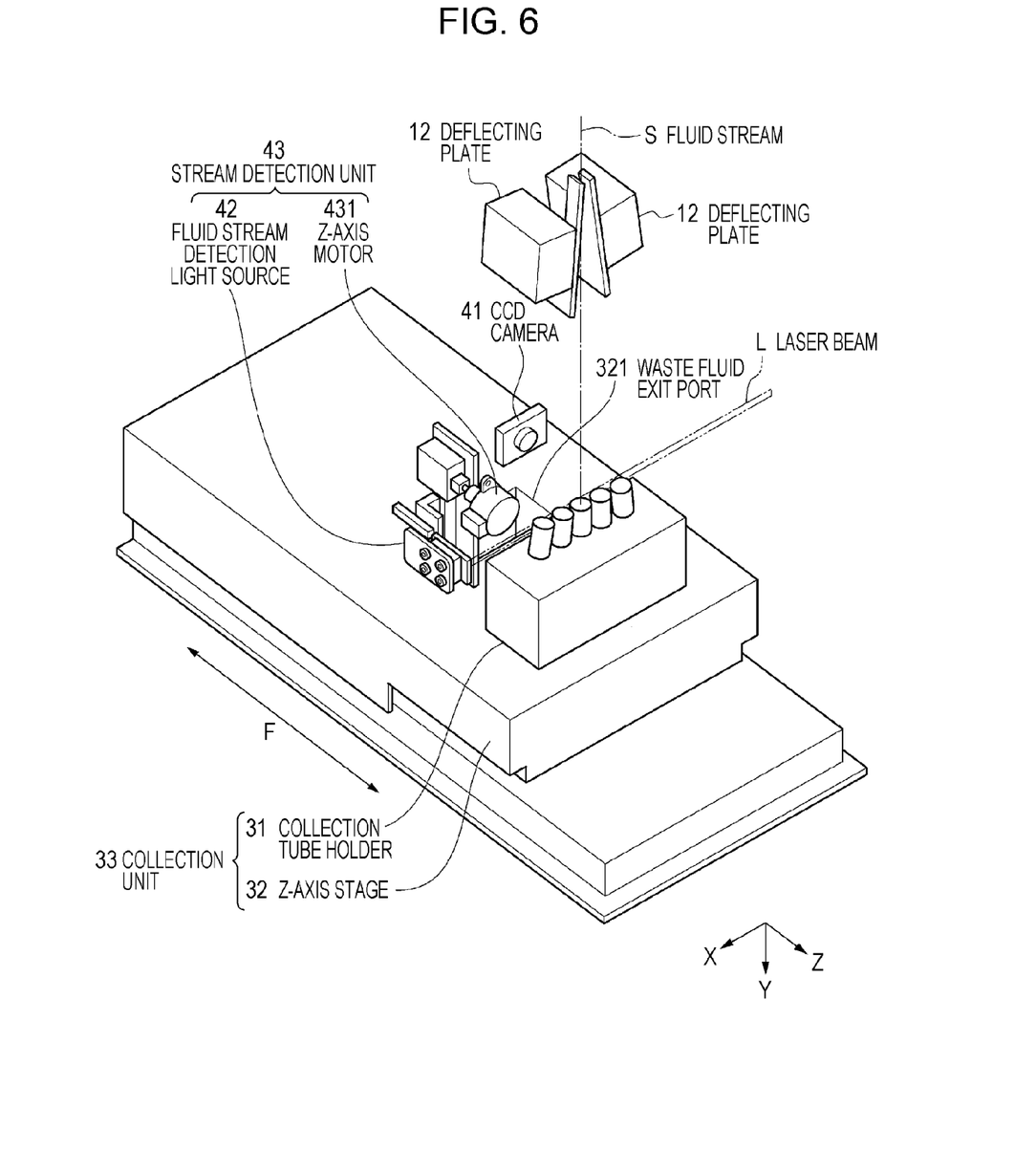
FIG. 6 schematically illustrates the position of the collection unit 33 when the fluid stream S is aligned with the collection tube 3 in the flow cytometer 1.

In Z-axis stage movement/position adjustment step $S_6$, the control unit adjusts the position of the collection tube holder 31 on the basis of the position information of the stream detection unit 43 in the Z-axis direction when the bright point is detected. More specifically, the position information of the stream detection unit 43 in the Z-axis direction is converted into the position information of the collection unit 33 in the same direction, and the Z-axis stage 32 is moved to the position corresponding to the converted position information. In this manner, the collection tube 3 disposed in the collection tube holder 31 is aligned with the fluid stream S in the Z-axis direction and, thus, the fluid stream S can accurately reach the collection tube 3. FIG. 6 illustrates the position of the collection unit 33 when the fluid stream S is aligned with the collection tube 3.

As described above, in the flow cytometer 1, the position of the collection tubes 3 is automatically adjusted with respect to the position of the fluid stream S. Accordingly, in the flow cytometer 1, the need for manual position adjustment of the microchip that is previously required each time the microchip is replaced with a new one or measurement is performed can be eliminated. Consequently, easy and highly accurate analysis can be performed.

Figure 7:
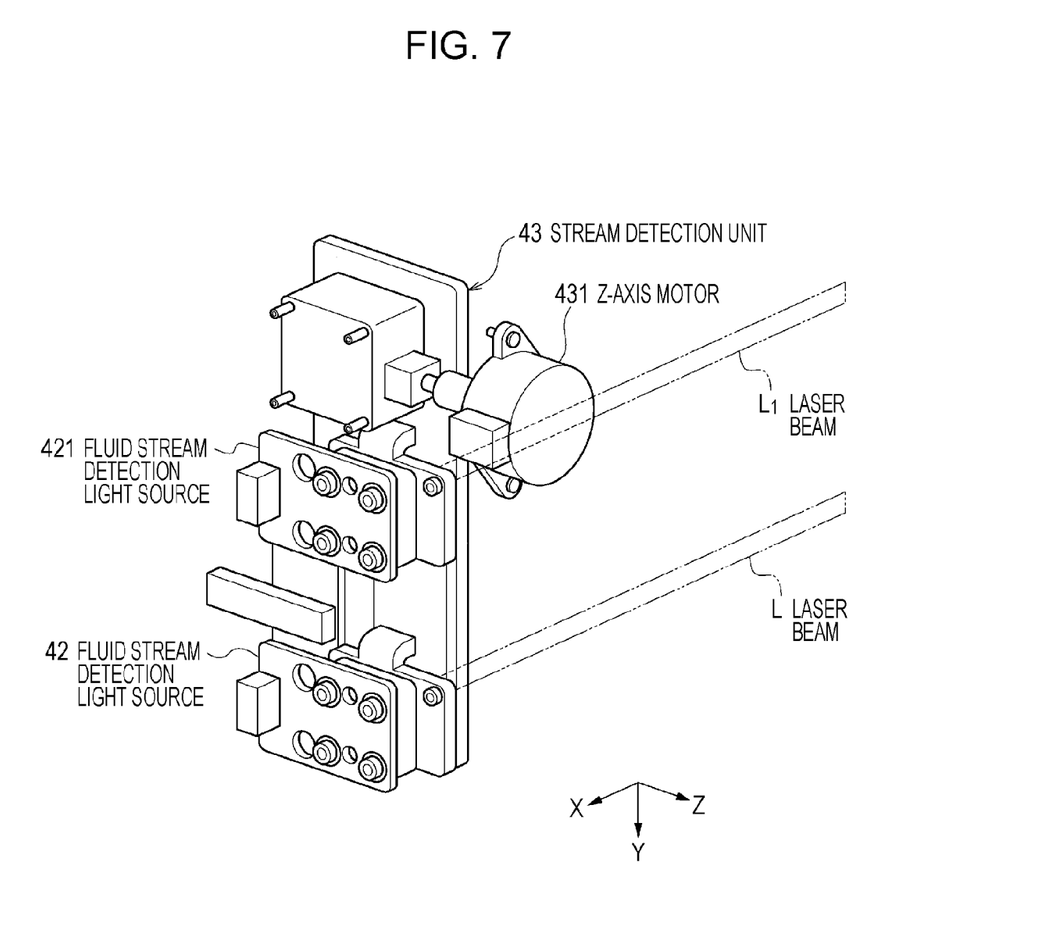
FIG. 7 illustrates a modification of the configuration of the stream detection unit 43 of the flow cytometer 1.

Note that in this example, the stream detection unit 43 includes only one fluid stream detection light source 42. However, in the flow cytometer 1, two or more fluid stream detection light source 42 may be disposed. FIG. 7 illustrates a configuration in which the stream detection unit 43 has a fluid stream detection light source 421 disposed therein in addition to the fluid stream detection light source 42. The fluid stream detection light source 421 is disposed so as to be separated from the fluid stream detection light source 42 in the direction of the fluid stream S (the Y-axis direction in the drawing). The fluid stream detection light source 421 outputs a laser beam $L_1$ that is parallel to the laser beam L output from the fluid stream detection light source 42. In this manner, by disposing a plurality of fluid stream detection light sources so as to be separated from each other in the Y-axis direction, one of the laser beams to be used can be selected in accordance with the height (the capacity) of each of the collection tubes 3 disposed in the collection container 31. More specifically, for example, for a 5-ml tube having a small height, the laser beam L of the fluid stream detection light source 42 is used. In contrast, for a 15-ml tube having a large height, the laser beam $L_1$ of the fluid stream detection light source 421 disposed at a higher position is used. In this manner, even when a tube having a large height is used, the occurrence of a situation in which the laser beam is blocked by the tube and, thus, position detection of the fluid stream S is unavailable can be prevented.

Figure 8:
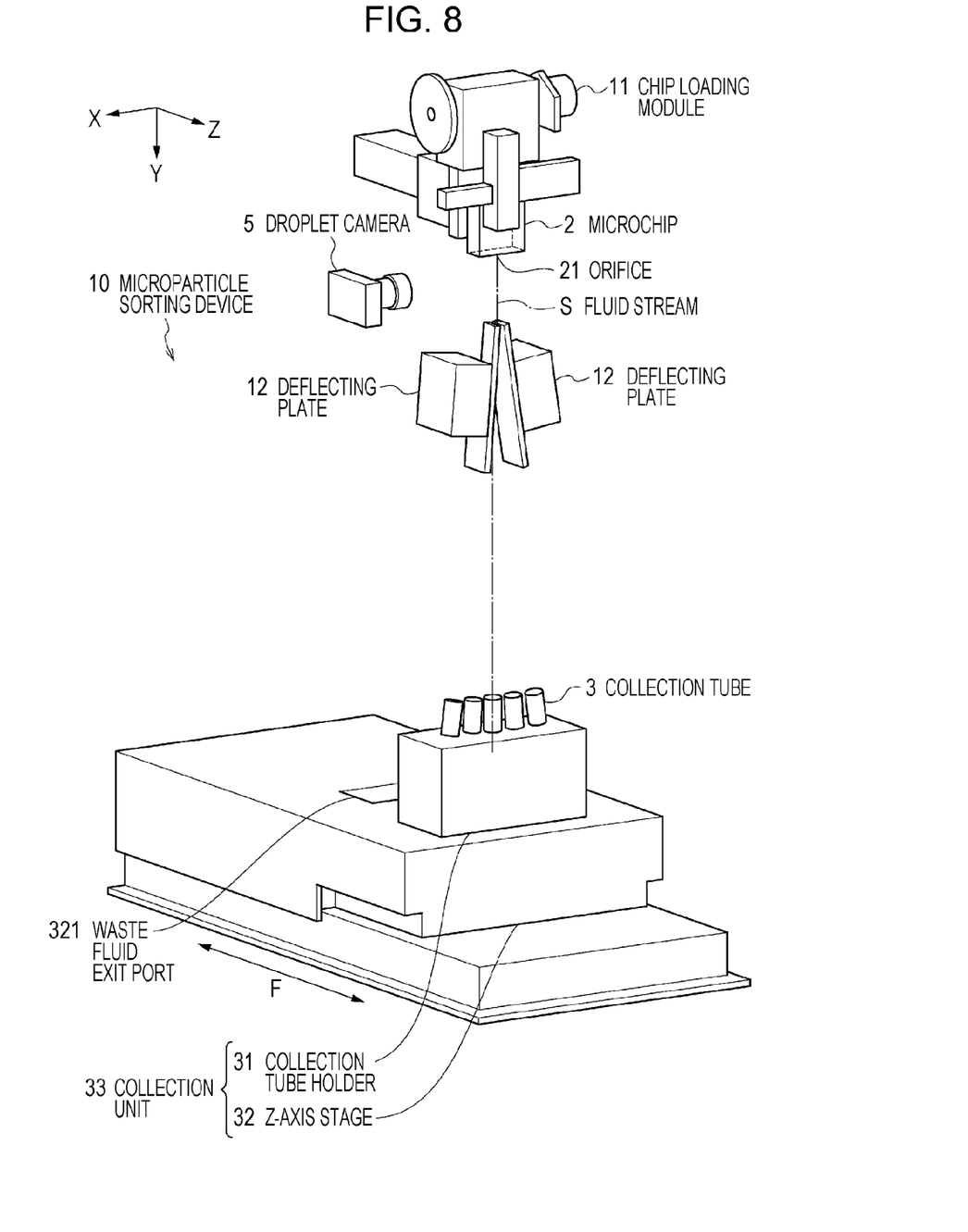
FIG. 8 is a schematic illustration of the configuration of a sorting system of a microparticle sorting device 10 (a flow cytometer 10) configured as a microchip type flow cytometer according to an embodiment related to the present technology.

3. Device Configuration of Microparticle Sorting Device According to Embodiment Related to Present Technology FIG. 8 is a schematic illustration of the configuration of a sorting system of a microparticle sorting device 10 (hereinafter also referred to as a "flow cytometer 10") according to an embodiment related to the present technology.

Unlike the flow cytometer 1 according to the above-described first embodiment, the flow cytometer 10 includes a droplet camera 5 instead of the CCD camera 41 and the stream detection unit 43 provided in the flow cytometer 1. The device configuration of the flow cytometer 10 other than the droplet camera 5 is the same as that of the flow cytometer 1 and, therefore, description of the configuration is not repeated. Note that in FIG. 8, the same reference symbols are used for the same configurations of the flow cytometer 10 as those of the flow cytometer 1 in FIG. 1.

The droplet camera 5 is a camera (e.g., a CCD camera) for capturing the image of the fluid stream S ejected from the orifice 21 of the microchip 2 or a discharged droplet. The image captured by the droplet camera 5 is displayed on, for example, a display unit. The image is used for user to be aware of the state of formation of the droplet in the orifice 2 (e.g., the size and the shape of the droplet and formation intervals).

As described above, the trajectories of the fluid stream S injected from the orifice 21 of the microchips 2 differ from one another due to individual difference in the microchip 2 mounted. Accordingly, each time the microchip 2 is replaced with a new one, the position of the fluid stream S may vary in the Z-axis direction (and the X-axis direction) in the drawing. In addition, even for the same microchip 2, the position of the fluid stream S may vary in each of measurements. In the flow cytometer 10, the droplet camera 5 also functions to detect such a variation of the position of the fluid stream S in the Z-axis direction.

Figure 9:
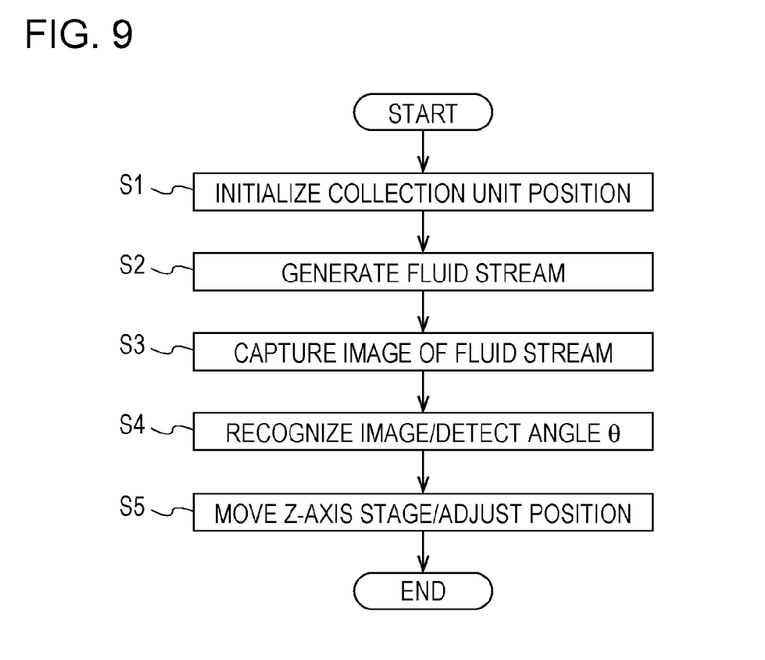
FIG. 9 is a flowchart illustrating a control step for adjusting the position of the fluid stream S and the position of the collection tube 3 in the flow cytometer 10.

4. Position Control Performed by Microparticle Sorting Device According to Related Embodiment Adjustment of the positions of the fluid stream S and the collection tube 3 using the droplet camera 5 and the collection unit 33 is described below. FIG. 9 is a flowchart illustrating a control step for adjusting the position of the fluid stream S and the position of the collection tube 3 in the flow cytometer 10. The control step includes the procedures of "collection unit position initialization step $S_1$", "fluid stream generation step $S_2$", "fluid stream imaging step $S_3$", "image recognition/ angle θ detection step $S_4$", and "Z-axis stage movement/ position adjustment step $S_5$". The procedures are described below.

(4-1) Collection Unit Position Initialization Step $S_1$/Fluid Stream Generation Step $S_2$ The procedures of Collection unit position initialization step $S_1$/fluid stream generation step $S_2$ are the same as those in the flow cytometer 1 according to the first embodiment. In these steps, the position of the collection unit 33 is initialized to the position at which the fluid stream S enters the waste fluid exit port 321 formed in the Z-axis stage 32. Thereafter, ejection of the fluid stream S is started.

(4-2) Fluid Stream Imaging Step $S_3$

In this step $S_3$, the control unit outputs a signal to the droplet camera 5. Upon receiving the signal, the droplet camera 5 captures the image of the fluid stream S.

(4-3) Image Recognition/Angle θ Detection Step $S_4$

Figure 10:
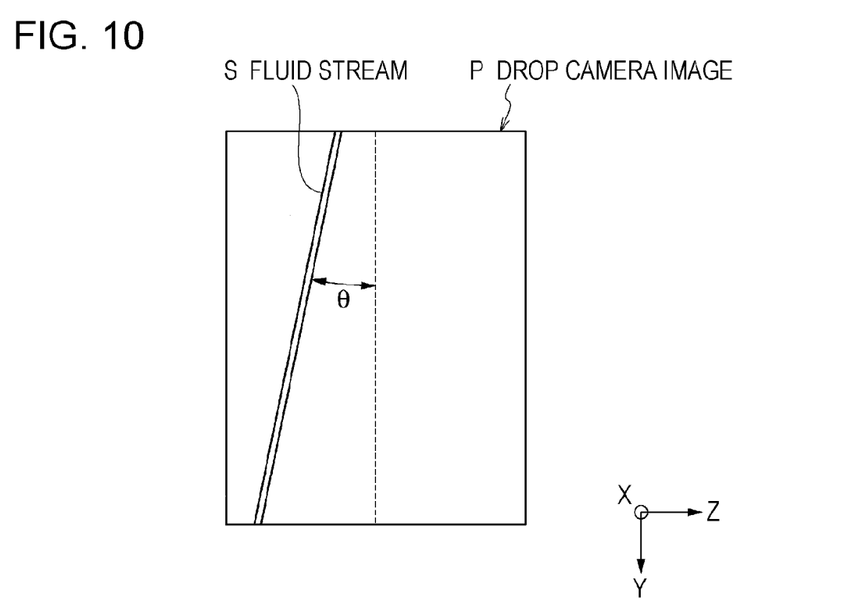
FIG. 10 is a schematic illustration of an example of an image captured by a droplet camera 5 of the flow cytometer 10.

The image of the fluid stream S captured by the droplet camera 41 is output to the control unit. An example of the image is illustrated in FIG. 10. In a droplet camera image P, the image of the fluid stream S is captured so as to be inclined at a certain angle θ with respect to the vertical direction. In image recognition/angle θ detection step $S_4$, the control unit performs image recognition and detects the angle θ from the droplet camera image P.

The angle θ corresponds to the output angle of the fluid stream S injected from the orifice 21. The variation of the trajectory of the fluid stream S injected from the orifice 21 is caused by the output angle θ of the fluid stream S injected from the orifice 21. Accordingly, by detecting the angle θ, the position information of the fluid stream S in the Z-axis direction can be obtained. To accurately detect the angle θ, it is more desirable that a plurality of the droplet cameras 5 be disposed so as to be separated from each other in the Y-axis direction and, thus, capture the images of the fluid stream S injected from the orifice 21 of the microchip 2 at a plurality of positions. By using the images of the fluid stream S captured at a plurality of positions, the angle θ can be more accurately calculated.

(4-4) Z-Axis Stage Movement/Position Adjustment Step $S_5$

In Z-axis stage movement/position adjustment step $S_5$, the control unit adjusts the position of the collection tube holder 31 on the basis of the detected angle θ. More specifically, the control unit moves the Z-axis stage 32 to an appropriate position calculated using the angle θ and a predetermined distance between the orifice 21 and the collection tube 3. In this manner, the collection tube 3 disposed in the collection tube holder 31 is aligned with the fluid stream S and, thus, the fluid stream S can accurately reach the collection tube 3.

As described above, in the flow cytometer 10, the position of the collection tubes 3 relative to the position of the fluid stream S is automatically adjusted. Accordingly, in the flow cytometer 10, the need for manual position adjustment of the microchip that is previously required each time the microchip is replaced with a new one or measurement is performed can be eliminated. Thus, easy and highly accurate analysis can be performed.

In addition, in the flow cytometer 10, automatic position adjustment of the fluid stream S and the collection tubes 3 can be provided using a device design that is simpler than that of the flow cytometer 1 according to the above-described first embodiment.

The microparticle sorting device according to the present technology can have the following configurations:

(1) A microparticle sorting device includes a pair of deflecting plates that face each other with a passage area of a fluid stream therebetween, a camera that captures the image of the fluid stream, and a fluid stream detection light source that emits light parallel to a direction in which the deflecting plate faces each other and that is movable in a direction perpendicular to the fluid stream and the light, (2) The microparticle sorting device described in the above (1) further includes a control unit that detects a bright point in an image captured by the camera through image recognition and stores the position of the fluid stream detection light source obtained when the image having the detected bright point therein is captured, (3) In the microparticle sorting device described in the above (2), a collection container that receives the fluid stream is mountable so as to be movable in the direction perpendicular to the fluid stream and the light, and the control unit adjusts the position of the collection container on the basis of the position of the fluid stream detection light source obtained when the image having the detected bright point therein is captured, (4) In the microparticle sorting device described in the above (2) or (3), the control unit moves the fluid stream detection light source in the direction perpendicular to the fluid stream and the light until the bright point is detected in an image captured by the camera, (5) In the microparticle sorting device described in any one of the above (1) to (4), a plurality of the fluid stream detection light sources are disposed so as to be separated from each other in the direction of the fluid stream, and (6) In the microparticle sorting device described in any one of the above (1) to (5), an orifice that generates the fluid stream is a microchip type flow cytometer provided in a microchip.

REFERENCE SIGNS LIST

1, 10 microparticle sorting device (flow cytometer)
11 chip loading module
12 deflecting plate
2 microchip
21 orifice
3 collection tube
31 collection tube holder
32 Z-axis stage
321 waste fluid exit port
33 collection unit
41 CCD camera
42, 421 fluid stream detection light source
43 stream detection unit
431 Z-axis motor
5 droplet camera
L, $L_1$ laser beam
S fluid stream

The invention claimed is:

1. A microparticle sorting device comprising:
a pair of deflecting plates that face each other with a passage area of a fluid stream therebetween, the fluid stream being ejected from a microchip through an orifice of the microchip;
a camera that captures an image of the fluid stream; and
a fluid stream detection light source that emits light parallel to a direction in which the deflecting plates face each other and that is movable in a direction perpendicular to the fluid stream and the light.

2. The microparticle sorting device according to claim 1, further comprising:
a control unit that detects a bright point in an image captured by the camera through image recognition and stores the position of the fluid stream detection light source obtained when the image having the detected bright point therein is captured.

3. The microparticle sorting device according to claim 1, wherein the fluid stream is ejected from the orifice as fluid droplets.

4. The microparticle sorting device according to claim 3, wherein the pair of deflecting plates applies electric force on the fluid droplets to control a movement direction of the fluid droplets.

5. A microparticle sorting device comprising:
a pair of deflecting plates that face each other with a passage area of a fluid stream therebetween;
a camera that captures an image of the fluid stream;
a fluid stream detection light source that emits light parallel to a direction in which the deflecting plates face each other and that is movable in a direction perpendicular to the fluid stream and the light; and
a control unit that detects a bright point in an image captured by the camera through image recognition and stores the position of the fluid stream detection light source obtained when the image having the detected bright point therein is captured, wherein a collection container that receives the fluid stream is mountable so as to be movable in the direction perpendicular to the fluid stream and the light, and wherein the control unit adjusts the position of the collection container on the basis of the position of the fluid stream detection light source obtained when the image having the detected bright point therein is captured.

6. The microparticle sorting device according to claim 5, wherein the control unit moves the fluid stream detection light source in the direction perpendicular to the fluid stream and the light until the bright point is detected in an image captured by the camera.

7. The microparticle sorting device according to claim 6, wherein a plurality of the fluid stream detection light sources are disposed so as to be separated from each other in the direction of the fluid stream.

8. The microparticle sorting device according to claim 7, wherein the microparticle sorting device comprises a flow cytometer.

9. A method for adjusting a position of a fluid stream and a position of a collection container for use in a microparticle sorting device, comprising the steps of:

emitting light that is parallel to a direction in which a pair of deflecting plates that face each other with a passage area of a fluid stream therebetween while moving the light in a direction perpendicular to the fluid stream and the light;

acquiring an image of the fluid stream;

detecting a bright point in the image through image recognition; and adjusting the position of the collection container that receives the fluid stream in the direction perpendicular to the fluid stream and the light on the basis of an irradiation position of the light obtained when the image having the detected bright point therein is acquired.

10. A microparticle sorting device comprising:

a pair of deflecting plates that face each other with a passage area of a fluid stream therebetween, the fluid stream comprising fluid droplets to which electric force is applied by the pair of deflecting plates;

a camera that captures an image of the fluid stream; and a fluid stream detection light source that emits light parallel to a direction in which the deflecting plate faces each other and that is movable in a direction perpendicular to the fluid stream and the light.

11. The microparticle sorting device according to claim 10, wherein the fluid stream is ejected from an orifice of a microchip.

* * * * *